March 19, 1974 B. J. MACHIN Plant Pat. 3,528
CHRYSANTHEMUM PLANT-EUROPA
Filed July 28, 1972
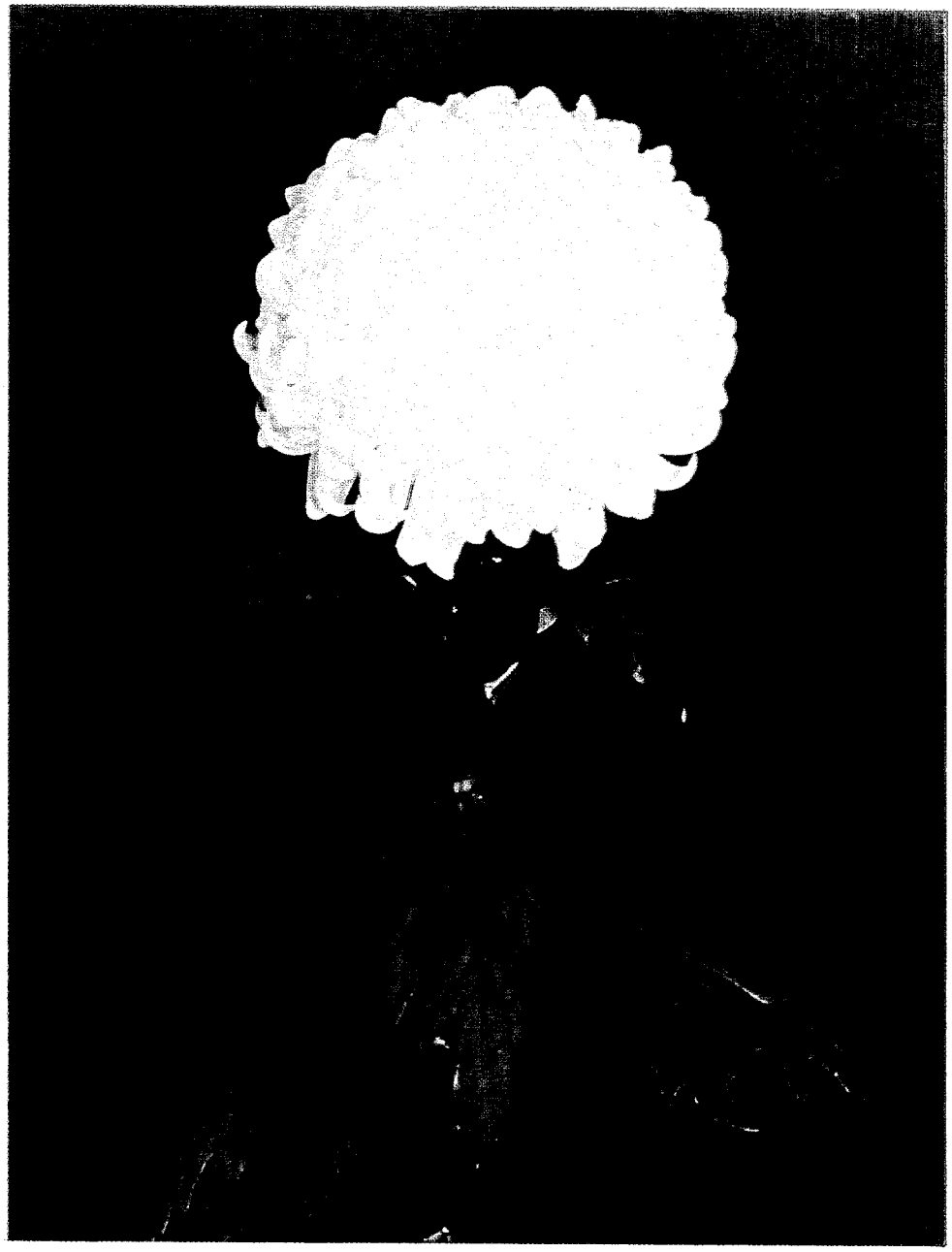

United States Patent Office

Plant Pat. 3,528
Patented Mar. 19, 1974

3,528
CHRYSANTHEMUM PLANT

Barrie John Machin, Arundel, England, assignor to Frampton's Nurseries Limited, Chichester, Sussex, England Filed July 28, 1972, Ser. No. 275,980
Int. Cl. A01h 5/00
U.S. Cl. Plt.—78 1 Claim This invention relates to a new and distinct variety of *Chrysanthenum morifolium* Bailey (standard type) known as Europa.

Europa is a sport found at Forbridge Nursery, Frampton's Nurseries Ltd., Runcton, Chichester, Sussex, England, in June 1970 from the variety Yellow Snowdon, described in U.S. patent application Ser. No. 171,781 filed Aug. 13, 1971, by William E. Duffett.

Yellow Snowdon is a yellow sport from the variety Snowdon, and the variety Snowdon was originated by me from a cross between a seedling 33D4 (which originated from a cross between the varieties Explorer and Jonquil) and the variety Columbia, the former being the seed parent and the latter being the pollen parent.

Europa has the following improved characteristics over the variety Yellow Snowdon.

(1) It is more vigorous and has slightly larger foliage. In order to produce flowers on a given length of stem Europa requires one week less of longday conditions for growth as compared with Yellow Snowdon.
(2) The flowering response of Europa is more uniform and slightly faster than Yellow Snowdon. Although both are classed as varieties of 10 week response, Europa will flower three days earlier in winter and one to two days earlier in summer than Yellow Snowdon.
(3) The flowers of Europa are paler than those of Yellow Snowdon and the bloom is much more incurving in form. Total bloom size of Europa is slightly larger than that of Yellow Snowdon. Also Europa contains more ray petals than Yellow Snowdon (approximately 280 to 250) and has a smaller percentage of disc petals. Europa rarely contains more than 10 percent disc petals. Yellow Snowdon at some seasons contains up to 30 percent disc petals.

The following characteristics distinguish Europa from Sunburst Mefo, the most similar yellow year round standard (other than Yellow Snowdon) grown in Great Britain of which I am aware:

(1) It is more responsive all year round. Europa will flower ten days earlier, winter or summer.
(2) The flowers are much more incurving in form.
(3) Production is more uniform and a higher percentage of marketable flowers is obtained.
(4) There are no problems with damping off of flowers under humid conditions.

Asexual reproduction of the variety Europa shows that the above characteristics are fixed and come true to type through succeeding generations.

The accompanying drawing shows a typical flower of my new variety depicted in color as nearly true as it is reasonably possible to make the same in a color illustration of this character.

The following is a detailed description of the new variety Europa with color terminology in accordance with the Royal Horticultural Society Colour Chart (RHS).

Genus: Chrysanthemum.
Species: *Morifolium* Bailey.
Type: Standard.
Class: Incurving decorative.
Breeding: Sport from Yellow Snowdon found in June 1970, in cultivated ground at Forbridge Nursery, Frampton's Nurseries, Ltd., Runcton, Chichester, Sussex.
Propagation: Holds its distinguishing characteristics through succeeding propagations by rooting vegetative shoots.
Bloom size:
*Average diameter.*—15 cm.
*Average depth.*—12 cm.
Petals: 270–300 ray florets. 30 disc florets.
*Form.*—Incurving decorative.
*Petals.*—Broad, overlapping, blunt, boat-shaped with medium texture.
Color of open bloom:
*Inner face of fully expanded petal.*—RHS 6C.
*Outer face of fully expanded petal.*—RHS 6D.
*Inner face of young petals.*—RHS 6C.
*Outer face of young petals.*—RHS 6D.
Response group: 10 weeks.
Temperature tolerance: 55–60° F. at night.
Plant: Wiry but strong upright habit of growth.
Foliage: Good quality. Medium size—medium texture—color, RHS 136A.
Stem: Average internode length, 3 cm. Medium thickness—strong and wiry. Color, RHS 146C. Water uptake, good.

I claim:

1. A new and distinct variety of *Chrysanthemum morifolium* Bailey, substantially as herein shown and described, characterized particularly as to novelty by the unique combination of a wiry, upright plant with incurving pale yellow flowers having 250 to 280 ray petals, about ten percent or less disc petals, and an average diameter of about 15 cm.

No references cited.

ROBERT E. BAGWILL, Primary Examiner